US012596111B2

(12) United States Patent　　(10) Patent No.: US 12,596,111 B2
Havenith et al.　　(45) Date of Patent: Apr. 7, 2026

(54) MEANS AND METHODS FOR DETECTING SOY ALLERGENS

(71) Applicant: Fraunhofer-Gesellschaft zur Förderung der angewandten Forschung e.V., Munich (DE)

(72) Inventors: Heide Havenith, Cologne (DE); Holger Spiegel, Aachen (DE); Stefan Schilberg, Aachen (DE); Elke Ueberham, Leipzig (DE); Jörg Lehmann, Borsdorf (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 1221 days.

(21) Appl. No.: 17/283,915

(22) PCT Filed: Oct. 11, 2019

(86) PCT No.: PCT/EP2019/077598
§ 371 (c)(1),
(2) Date: Apr. 8, 2021

(87) PCT Pub. No.: WO2020/074704
PCT Pub. Date: Apr. 16, 2020

(65) Prior Publication Data
US 2021/0382028 A1　　Dec. 9, 2021

(30) Foreign Application Priority Data
Oct. 11, 2018　(DE) .......................... 102018217447.4

(51) Int. Cl.
*G01N 33/92* (2006.01)
*C07K 16/16* (2006.01)
*G01N 33/02* (2006.01)

(52) U.S. Cl.
CPC ........... *G01N 33/025* (2013.01); *C07K 16/16* (2013.01)

(58) Field of Classification Search
CPC ...... G01N 33/025; C07K 16/16; C12N 15/09; C12N 15/61; C12N 15/63; C12N 15/66; C12N 5/10
See application file for complete search history.

(56) References Cited

U.S. PATENT DOCUMENTS 5,850,016 A * 12/1998 Jung .................. C12N 15/8254
536/23.6
2005/0025768 A1 * 2/2005 De Fougerolles ...... A61P 37/00
435/7.1

FOREIGN PATENT DOCUMENTS

WO　WO 1997/035023 A2　9/1997
WO　WO 2007/095304 A2　8/2007

OTHER PUBLICATIONS

Lin et al., Biochimica Biophysica Acta, 2004, 1698:203-212.*
Abbot et al., "Validation Procedures for Quantitative Food Allergen ELISA Methods: Community Guidance and Best Practices," Journal of AOAC International, vol. 93, No. 2, 442-450, (2010).
Boes et al., "Affinity Purification of a Framework 1 Engineered Mouse/Human Chimeric IgA2 Antibody From Tobacco," Biotechnology and Bioengineering, vol. 108, No. 12, 2804-2814, (2011).
Cucu et al., "ELISA-Based Detection of Soybean Proteins: A Comparative Study Using Antibodies Against Modified and Native Proteins", Food Analytical Methods, vol. 5, No. 5, pp. 1121-1130, (2011).
Database Nucleotide, "Glycine max 2S albumin pre-propeptide mRNA, complete cds", retrieved from NCBI Database accession No. AF005030, (1997).
Database UniProt, retrieved from EBI accession No. UNIPROT: P19594, Database accession No. P19594, (1991).
Ebisawa et al., Gly m 2S albumin is a major allergen with a high diagnostic value in soybean-allergic children, Journal of Allergy and Clinical Immunology, vol. 132, No. 4, pp. 976-978, (2013).
Feller et al., "Plant-Based Production of Recombinant Plasmodium Surface Protein Pf38 and Evaluations of its Potential as a Vaccine Candidate," PlosOne, vol. 8, Issue 11, e79920, (2013).
Geng et al., "Development of a Sandwich ELISA for Quantification of Gly m 4, a Soybean Allergen", Journal of Agricultural and Food Chemistry, vol. 63, No. 20, pp. 4947-4953, (2015).
Gonzalez et al., "Monoclonal antibody-based method to quantify Gly m 1. Its application to assess environmental exposure to soybean dust", Allergy, vol. 55, pp. 59-64, (2000).
Klemans et al., "Components in soy allergy diagnostics: Gly m 2S albumin has the best diagnostic value in adults", Allergy, vol. 68, No. 11, pp. 1396-1402, (2013).
Lacorn et al., "Accurate and Sensitive Quantification of Soy Proteins in Raw and Processed Food by Sandwich ELISA," Food Science and Technology, 4(4), S. 69-77, (2016).
Lin et al., "The Potential Allergenicity of Two 2S Albumins from Soybean (*Glycine max*): A Protein Microarray Approach," Int Arch Allergy Immunol, 141, 91-102, (2006).
Meinlschmidt et al., "Enzymatic treatment of soy protein isolates: effects on the potential allergenicity, technofunctionality, and sensory properties," Food Science & Nutrition, 4(1), 11-23, (2016).

(Continued)

*Primary Examiner* — Hong Sang
(74) *Attorney, Agent, or Firm* — KNOBBE, MARTENS, OLSON & BEAR, LLP

(57) ABSTRACT

The present invention relates to the field of antibodies and their application in food and feedstuff quality control. In particular, the invention relates to a method for the manufacture of an antibody that specifically binds to soy Gly m 8 protein wherein said method comprises immunising an animal with the purified soy Glym8 protein, wherein said soy Glym8 protein has been obtained by expressing soy Glym8 protein in plants, and preferably, tobacco plants and purifying the soy Glym8 protein from said plants and, preferably, tobacco plants and obtaining an antibody from the animal which specifically bind to soy Gly m8 protein, wherein the animal will be sacrificed. Moreover, the invention contemplates an antibody obtained by said method as well as the use of said antibody for detecting soy material in a food preparation or feedstuff preparation. Further, a method for detecting soy material in a food preparation or feedstuff preparation and a kit for carrying out said method are provided.

12 Claims, 8 Drawing Sheets

Figure 1:
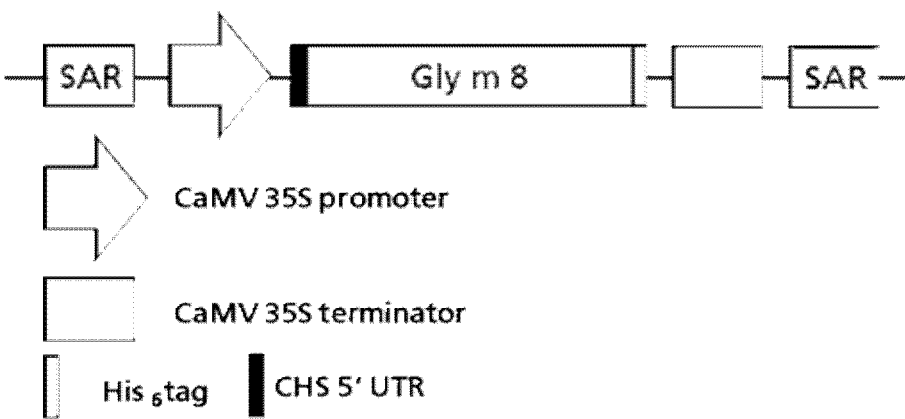
Figure 1:
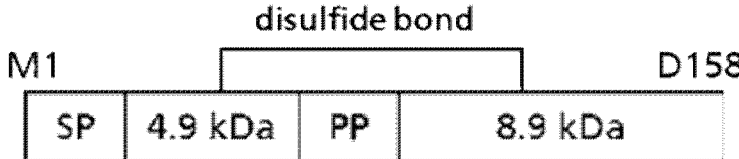
Figure 1:
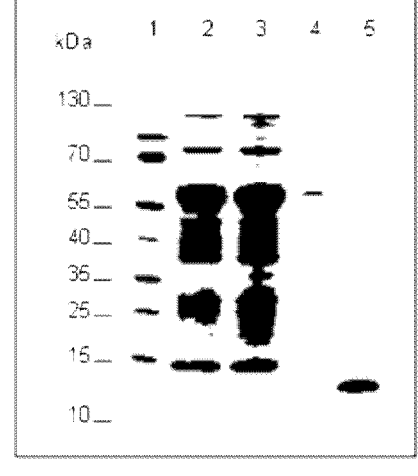
Figure 1:
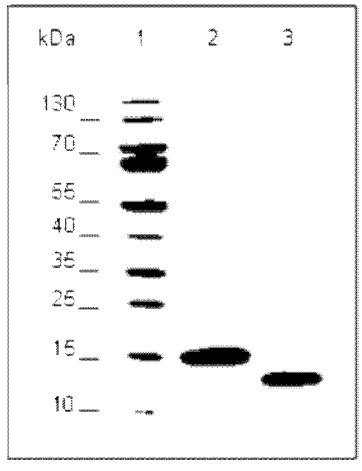

Specification includes a Sequence Listing.

(56) References Cited

OTHER PUBLICATIONS

Meinlschmidt et al., "Immunoreactivity, sensory ad physicochemical properties of fermented soy protein isolate," Food Chemistry 205, S. 229-238, (2016).

Meinlschmidt et al., "High Pressure processing assisted enzymatic hydrolysis—An innovative approach for the reduction of soyimmunoreactivity," Innovative Food Science and Emerging Technologies, 2017, 58-67, (2016).

Maruyama, Nobuyuki et al., "Gly m 5/Gly m I fusion component as a potential novel candidate molecule for diagnosing soya bean allergy in Japanese children," Clinical & Experimental Allergy 48(12), S. 1726-1734, (2018).

Needleman, et al., A general method applicable to the search for similarities in the Amino Sequence of two proteins, J. Mol. Biol., vol. 48, pp. 443-453, 1970.

Pavlicevic et al., "Influence of extraction method on protein profile of soybeans", Hem Ind 67 (4), S. 687-694, (2013).

Pearson et al, Improved tools for biological sequence comparison, Proc. Natl. Acad Sci. (USA), vol. 85, pp. 2444-2448, 1988.

Sack et al., "Functional analysis of the broadly neutralizing human anti-HIV-1 antibody 2F5 produced in transgenic BY-2 suspension cultures", The FASEB Journal vol. 21, No. 8, pp. 1655-1664, (2007).

Seber et al., "Scalable Purification and Characterization of the Anticancer Lunasin Peptide from Soybean", PLOS ONE, vol. 7, No. 4, pp. 1-13, (2012).

Smith, et al., Comparison of Blosequences, Add. Apl. Math. vol. 2, pp. 482-489, 1981.

Taylor et al., "Allergen immunoassays—considerations for use of naturally incurred standards", Analytical and Bioanalytical Chemistry, vol. 395, No. 1, pp. 83-92, (2009).

Ueberham et al., "Simplified Tracking of a Soy Allergen in Processed Food Using a Monoclonal Antibody-Based Sandwich ELISA Targeting the Soybean 2S Albumin Gly m 8", Journal of Agricultural and Food Chemistry, vol. 67, No. 31, pp. 8660-8667, (2019).

Galvez et al., "The Electronic Plant Gene Register", Plant Physiol., 114: 1567-1569, (1997).

International Preliminary Report of Patentability and Written Opinion received in PCT Application No. PCT/EP2019/077598 mailed on Apr. 22, 2021.

International Search Report and Written Opinion in International Application No. PCT/EP2019/077598 dated Jan. 15, 2020.

* cited by examiner

A

C                                          D

Fig. 8

A)

ATGGGCACCAAGTTCACAATCCTCCTCATCTCTCTTCTCTTCTGCATCGCCCACACTTGC

AGCGCCTCCAAATGGCAGCACCAGCAAGATAGCTGCCGCAAGCAGCTCCAGGGGGTGAAC

CTCACGCCCTGCGAGAAGCACATCATGGAGAAGATCCAAGGCCGCGGCGATGACGATGAT

GATGATGACGACGACAATCACATTCTCAGGACCATGCGGGGAAGAATCAACTACATAAGG

AGGAACGAAGGAAAAGACGAAGACGAAGAAGAAGAAGGACACATGCAGAAGTGCTGCACA

GAAATGAGCGAGCTGAGAAGCCCCAAATGCCAGTGCAAAGCGCTGCAGAAGATAATGGAG

AACCAGAGCGAGGAACTGGAGGAGAAGCAGAAGAAGAAAATGGAGAAGGAGCTCATTAAC

TTGGCTACTATGTGCAGGTTTGGACCCATGATCCAGTGCGACTTGTCCTCCGATGAC

B)

MTKFTILLIS LLFCIAHTCS ASKWQHQQDS CRKQLQGVNL TPCEKHIMEK IQGRGDDDDD
DDDDNHILRT MRGRINYIRR NEGKDEDEEE EGHMQKCCTE MSELRSPKCQ CKALQKIMEN
QSEELEEKQK KKMEKELINL ATMCRFGPMI QCDLSSDD

MEANS AND METHODS FOR DETECTING SOY ALLERGENS

REFERENCE TO SEQUENCE LISTING

The present application is being filed along with a Sequence Listing in electronic format. The Sequence Listing is provided in a file entitled 2021-03-22_Sequence_Listing_HRZG001.014APC.TXT, which was created on Mar. 22, 2021 and is approximately 3 kilobytes in size. The information in the electronic Sequence Listing is hereby expressly incorporated by reference in its entirety.

FIELD

The present invention relates to the field of antibodies and their application in food and feedstuff quality control. In particular, the invention relates to a method for the manufacture of an antibody that specifically binds to soy Gly m 8 protein wherein said method comprises immunising an animal with the purified soy Gly m8 protein, wherein said soy Gly m8 protein has been obtained by expressing soy Gly m8 protein in plants, and preferably, tobacco plants and purifying the soy Gly m8 protein from said plants and, preferably, tobacco plants and obtaining an antibody from the animal which specifically bind to soy Gly m8 protein, wherein the animal will be sacrificed. Moreover, the invention contemplates an antibody obtained by said method as well as the use of said antibody for detecting soy material in a food preparation or feedstuff preparation. Further, a method for detecting soy material in a food preparation or feedstuff preparation and a kit for carrying out said method are provided.

BACKGROUND

Over the last decades, the detection of soy in food samples is realized using enzyme-linked immunosorbent assays (ELISA) based on polyclonal antibodies either against whole soy protein extracts or isolated components known to be extraordinarily stable. To date, the only specified targets for detection of soy material which are stated by manufacturers in commercial ELISAs are either the trypsin inhibitor Gly m TI or one of the highly abundant soybean storage proteins Gly m 5 or Gly m 6. In near future a multitude of plant proteins will be entering the food chain, because there is a strong demand for substitutes to animal proteins in food. But just, most popular and sophisticated protein ingredients of plant origin, lupin and soy, are counted among allergenic food ingredients and have to be declared when added to processed food even in traces. This will pose new challenges to allergen detection and quantification, especially to soy analyses by ELISA because current assays addressing Gly m TI are not able to distinguish between different bean species and soy. Tests detecting Gly m 6, in turn, display high cross-reactivity to pea (Lacorn et al. 2016, fst 4 (4), S. 69-77).

Gly m 8 represents a 2S albumin of soybean, *Glycine max*, not addressed in the context of allergen detection before. However, Gly m 8 has been shown to be the most important predictor for severity of allergic reactions in children so far (Ebisawa et al. 2013, The Journal of allergy and clinical immunology 132 (4), 976-8). The particular three-dimensional molecular structure of the 2S albumins in general is supposed to trigger their allergenicity. Both, thermal stability and resistance to complete digestion in the gastrointestinal tract are important features of several food allergens.

Recently, a sandwich ELISA using various anti-Gly m 5 antibodies (Meinlschmidt et al. 2016, Food chemistry 205, S. 229-238) was established but it was realized that relative quantities of native and denatured Gly m 5 fractions extracted from complex food and highly processed protein ingredients using different extraction methods varied significantly leading mainly to underestimation of the true Gly m 5 content.

SUMMARY

The technical problem underlying the present invention may be seen as the provision of means and methods for complying with the aforementioned needs. The technical problem is solved by the embodiments characterized in the claims and herein below.

The present invention relates to a method for the manufacture of an antibody that specifically binds to soy Gly m 8 protein wherein said method comprises:
- a) immunising an animal with the purified soy Gly m8 protein, wherein said soy Gly m8 protein has been obtained by
  - i) expressing soy Gly m8 protein in plants and, preferably, tobacco plants; and
  - ii) purifying the soy Gly m8 protein from said plants and, preferably, tobacco plants;
  and
- b) obtaining an antibody from the animal which specifically bind to soy Gly m8 protein,
wherein the animal will be sacrificed.

DESCRIPTION

The term "antibody" as used herein refers to any type or class of antibody including naturally occurring antibodies such as polyclonal antibody sera or monoclonal antibodies. However, an antibody as referred to herein may also be any derivative or variant of such antibodies, preferably, a humanized or chimeric antibody, a single chain antibody, antibody fragments and the like. Antibody fragments and derivatives comprised by the term antibody as used herein encompass a bispecific antibody, a synthetic antibody, an Fab, F(ab)2, Fv, nanobodies or scFv fragment, or a chemically modified derivative of any of these antibodies.

Moreover, the antibody of the present invention may be coupled to a detectable label. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BLIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemiluminescence, which can be measured according to methods known in the art (e.g. using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include 35S, 125I, 32P, 33P and the like. A radioactive label can be detected by any method known and appropriate, e.g. a light-sensitive film or a phosphor imager.

Yet, the antibody may be detectable in that it can be specifically bound by a secondary antibody. Such a secondary antibody may also be a polyclonal or monoclonal antibody or any derivative thereof as specified elsewhere herein. Further, if a secondary antibody is used for detecting the primary antibody which specifically recognizes the Gly m 8 protein, it will be understood that the said secondary antibody may be coupled to a detectable label as specified above.

Specific binding as used in the context of the antibody of the present invention means that the antibody does not cross react with other polypeptides. Specific binding can be tested by various well known techniques. Antibodies or fragments thereof, in general, can be obtained by using methods described in standard text books of molecular biology. Preferably, the antibody which specifically binds to the soy Gly m8 protein in accordance with the present invention exhibits no cross reactivity for proteins from wheat, celery, mustard, peanut, black beans, mungo beans, white beans, quail beans, lupines, field bean and pea. Also preferably, it has a KD of at least 1.57×10-10 for the soy Gly m8 protein.

The skilled artisan is well aware of how theses properties can be tested, preferably, as described in the accompanying Examples, below.

Monoclonal antibodies can be prepared by the techniques which comprise the fusion of mouse myeloma cells to spleen cells derived from immunized animals and, preferably, immunized mice. Preferably, an immunogenic Gly m 8 protein or peptide is administered to a mammal. The said peptide may be, preferably, conjugated to a carrier protein, such as bovine serum albumin, thyroglobulin, and keyhole limpet hemocyanin (KLH). Depending on the host species, various adjuvants can be used to increase the immunological response. Such adjuvants encompass, preferably, Freund's adjuvant, mineral gels, e.g., aluminum hydroxide, and surface active substances, e.g., lysolecithin, pluronic polyols, polyanions, peptides, oil emulsions, keyhole limpet hemocyanin, and dinitrophenol. Monoclonal antibodies which specifically bind to the Gly m 8 protein can be subsequently prepared using the well known hybridoma technique, the human B cell hybridoma technique or the EBV hybridoma technique.

The term "plants" as used herein refers to plants which do not naturally express proteins with highly related immunological properties compared to the soy Gly m 8 protein which could potentially elicit cross-reactivity if present as impurities in recombinant soy Gly m 8 protein preparations. Preferably, plants are tobacco plants.

In accordance with the method of the present invention, the Gly m 8 protein used for immunising the animal has been obtained from tobacco plants. Preferably, the Gly m8 protein is expressed from a suitable expression construct in tobacco plants. The expression construct, preferably, comprises a nucleic acid which encodes soy Gly m8 protein and, more preferably, soy Gly m 8 comprising the signal peptide and the pro-peptide of soy Gly m8, i.e. amino acids M1 to D158 of the soy Gly m 8 protein (UniProt ID: P19594 or SEQ ID NO: 2). The Soy Gly m 8 protein as referred to in accordance with the present invention encompasses the *Glycine* may Gly m 8 protein having the sequence as deposited under the aforementioned UniProt ID: P19594. However, also comprised as soy Gly m8 proteins according to the present invention are variants of said specific protein. Variants as referred to herein are Gly m 8 proteins from soy which differ in their amino acid sequence due to naturally or non-naturally mutations. Typically, a variant Gly m8 protein exhibits, however, essentially the same biological and/or immunological properties than the specific Gly m 8 protein referred to above. Preferably, a variant Gly m 8 protein has an amino acid sequence which has an amino acid sequence compared to the specific soy Gly m 8 protein referred to above being at least 70%, at least 80%, at least 90%, at least 95%, at least 97%, at leastz 98%, at least 99% identical. Sequence identity as referred to herein may be determined by well known techniques in the art. Typically, the sequences to be compared to each other are compared over their entire length or over the at least 50% of their sequences. Optimal alignment of sequences for comparison may be conducted by the local homology algorithm disclosed by Smith 1981, Add. APL. Math. 2:482, by the homology alignment algorithm of Needleman 1970, J. Mol. Biol. 48:443, by the search for similarity method of Pearson 1988, Proc. Natl. Acad Sci. (USA) 85: 2444, by computerized implementations of these algorithms (GAP, BESTFIT, BLAST, FAST, PASTA, and TFASTA in the Wisconsin Genetics Software Package, Genetics Computer Group (GCG), 575 Science Dr., Madison, WI), or by visual inspection. Moreover, the said nucleic acid sequence is, preferably, codon-optimized for expression in tobacco plants (see, preferably, SEQ ID NO: 1). Moreover, the soy Gly m 8 protein encoding nucleic acid may be fused to a nucleic sequence encoding a purification tag. Suitable purification tags are well known in the art and comprise, e.g., the FLAG-tag, the His6-tag, MYC-tag and others. Thus, the soy Gly m 8 protein, preferably, further comprises a purification tag.

Moreover, the expression construct for soy Gly m 8 protein in tobacco plants shall further comprise a promoter which allows for expression of the soy Gly m 8 protein in tobacco plants. A suitable promoter may be a ubiquitously expressing promoter, such as the CaMV 35 S promoter, or a promoter which allows for tissue specific expression. Further, it may be an inducible promoter. Preferably, the expression construct used for the soy Gly m8 protein is the pTRAkt vector described in the accompanying Examples, below. Thus, the said soy Gly m 8 protein is expressed from an expression construct that has been introduced into the tobacco plants and wherein the coding nucleic acid sequence for the soy Gly m 8 protein has been codon-optimized for tobacco plants.

Subsequently, the recombinantly produced protein will be subsequently purified. For purification, tobacco plants or parts thereof may be harvested which recombinantly express the Gly m 8 protein as specified above. Proteins shall be extracts from the plants or plant parts. Subsequently, affinity chromatography may be performed for obtaining fractions comprising the recombinantly produced Gly m 8 protein. Preferably, purification tag-based affinity chromatography shall be applied. More preferably, the affinity chromatography is performed as described in the accompanying Examples, below. After affinity purification of the recombinant soy Gly m 8 protein, further purification may be necessary. To this end, size exclusion chromatography or other measures may be applied well known to the skilled person and, more preferably, the further purification is carried out as described in the accompanying Examples, below. Purity of the recombinant Gly m 8 protein may be investigated by gel chromatography, in particular by SDS PAGE. Thus, preferably, said purifying referred to in the method of the present invention comprises at least one step of affinity purification of the soy Gly m8 protein and/or at least one step of size-exclusion purification of the soy Gly m8 protein.

Further, the method of the invention comprises the step of immunising an animal with the soy Gly m8 protein obtained as described before. The animal will be kept under conditions and for a time sufficient to produce an antibody titer against the soy Gly m8 protein which is sufficiently such that the antibody can be obtained or such that donor spleenocytes can be obtained for hybridoma production. Preferably, the production of hybridomas is envisaged according to the present invention. However, also a polyclonal antiserum comprising antibodies which specifically bind to the soy Gly m 8 protein referred to above may be obtained in some embodiments. Monoclonal antibody-producing hybridomas may be obtained by fusing spleenocytes from the immunized animal, preferably a mouse, to myeloma cells by techniques well known in the art. Details are, preferably, found in the accompanying Examples, below. The resulting hybridomas will be selected and those which produce monoclonal antibodies with the desired immunological properties referred to elsewhere herein will be cultured for antibody production. The desired antibodies can be obtained from the culture media by techniques well known to the skilled artisan and described in the accompanying Examples, below. Thus, said obtaining an antibody from the animal, preferably, comprises generating hybridomas from the animal and selecting and cultivating a hybridoma clone which produces an antibody which specifically binds to soy Gly m8 protein.

It will be understood that the animal used for the antibody production, in any event, will be sacrificed. Accordingly, the method of the present invention can not be considered whatsoever as a therapeutic method practiced on the animal body nor as a method of surgery improving life quality of the animal.

The term "animal" as used herein relates to animals suitable for antibody production. Humans are not considered as such animals. Typically, the animal is a laboratory animal such as a rabbit, goat, sheep or mouse. For the production of monoclonal antibodies, mice are envisaged as animals. More preferably, details on suitable animals are found in the accompanying Examples, below.

Advantageously, it has been found in the studies underlying the present invention that highly specific monoclonal antibodies for soy Gly m 8 protein can be obtained when using recombinant soy Gly m 8 protein produced in transgenic tobacco plants. The goal of the study was to develop an ELISA based on Gly m 8-specific monoclonal antibodies (mAb) and to validate its reliability as indicator for traces of soy proteins in food and feedstuff preparations. The anti-Gly m 8-specific mAbs complement a larger set of anti-soy protein antibodies generated for detection and quantification of the water-soluble soy proteins Gly m 4 and Gly m TI in soy protein preparations developed in our group (unpublished data).

In the studies underlying the present invention an ELISA with recombinant Gly m 8 protein as internal calibration standard and mAbs to guarantee maximum invariability of the assay was developed. Detailed characterization of activity and binding parameters of the antibodies using surface plasmon resonance spectroscopy (SPR) provided efficient control for quality of test components.

Soy Gly m 8 as a 2S albumins is a promising target in allergen analytics. Gly m 8 has been shown to be the most important predictor for severity of allergic reactions in children so far. Its extraordinary stability allows for using this allergen as an indicator even in heavily treated food or feedstuff preparation. Another benefit using Gly m 8 in ELISA applications is its excellent solubility in water and low salt buffers thus making extraction even from complex food very fast and simple. In contrast, extraction of the main storage proteins from *Glycine max* Gly m 6 or Gly m 5 with even allergenic potential is much more time consuming and error-prone. Thus, an antibody which specifically binds to soy Gly m8 protein will greatly improve quality control of food and feedstuff preparations for the presence of allergenic components such as soy allergens. Moreover, the antibodies against soy Gly m 8 protein according to the present invention unlike those against soy Gly m 6 or Gly m 5 proteins exhibit no or reduced cross-reactivity for other bean family proteins. Finally, unlike soy Gly m Ti protein being a trypsin inhibitor which is typically excluded from food or feedstuff preparations at an early stage in their manufacture, soy Gly m8 protein is typically maintained in the said preparations. A further advantage of using recombinant soy Gly m 8 protein from transgenic tobacco plants is that the protein itself can be provided in highly standardized form and, thus, be used as reliable reference standards for detection assays as described below.

In the following, further embodiments of the invention will be descried. The explanations and definitions of the terms made above apply mutatis mutandis for these embodiments.

The present invention further relates to an antibody which specifically binds to soy Gly m8 protein wherein said antibody has been obtained by the method of the present invention. Preferably, said antibody is a monoclonal antibody as specified elsewhere herein in detail.

The present invention further contemplates the use of an antibody of the invention for detecting the presence of soy material in a food preparation or feedstuff preparation.

The term "food preparation" as used herein refers to any food product which typically comprises or is suspected to comprise soy material. The soy material may be included in the preparation on purpose or may be an impurity, e.g., as the result of the food preparation manufacturing process. It will be understood that the food preparation shall not comprise or be suspected to comprise soy material that is essentially free or which has been artificially depleted of soy Gly m 8 protein.

The term "feedstuff preparation" as used herein refers to any feedstuff product which typically comprises or is suspected to comprise soy material. The soy material may be included in the preparation on purpose or may be an impurity, e.g., as the result of the manufacturing process for the preparation. It will be understood that the feedstuff preparation shall not comprise or be suspected to comprise soy material that is essentially free or which has been artificially depleted of soy Gly m 8 protein.

As described before, allergens in food and feedstuff preparations are typically to be determined in quality controls. The reason for determining these allergens is that in light of their allergenic potential and the great prevalence of food allergies they must be declared as a safety measure, in particular, in food preparations. Accordingly, it will be understood that the antibody of the present invention can be used for said purpose, preferably, by applying a method for detecting soy material in a food preparations or feedstuff preparations as specified elsewhere herein.

Moreover, the present invention relates to a method for detecting soy material in a food preparation or feedstuff preparation comprising the steps of:

a) contacting a sample of the food preparation or feedstuff preparation with the antibody of the present invention under conditions and for a time sufficient to allow specific binding of said antibody to soy Gly m8 protein comprised in the soy material; and b) determining the antibody-soy Gly m8 protein complex formed upon specific binding of the antibody to the soy Gly m8 protein in step a); and c) detecting the soy material in the food preparation or feedstuff preparation if the antibody-soy Gly m8 protein complex was determined in step b).

The term "detecting soy material in food preparation or feedstuff preparation" refers to qualitative detecting the presence or absence of such soy material as indicated by the presence of the soy Gly m 8 protein. Moreover, the term also comprises quantitatively or semi-quantitatively determining the amount of soy material present in the preparation. It will be understood, however, that the detection of the soy material according to the method of the present invention depends on the presence of soy Gly m8 protein in the soy material. Accordingly, if none or not enough soy Gly m 8 protein (below the detection limit) is present in the soy material, the method may not work properly. However, it is envisaged that the method of the present invention will provide reliable results at least within the detection limits of an individual antibody applied. The detection limits can be determined by the skilled person without further ado, e.g., as described in the accompanying Examples, below.

It will be understood that for the quantification of soy material, it may be necessary to establish a calibration for the detection method using, e.g., standardized predefined recombinant soy Gly m 8 protein as described elsewhere herein. The skilled person is well aware of how such calibration may be carried out.

In a first step of the method for detecting, a sample of the food preparation or feedstuff preparation is brought into contact with the antibody of the present invention under conditions and for a time sufficient to allow specific binding of said antibody to soy Gly m8 protein comprised in the soy material. Typically, the food or feedstuff preparation or a sample thereof is dissolved in an aqueous solution. Subsequently, the antibody is added to said solution and incubated for a time and under conditions sufficient to allow specific binding. How to adjust suitable conditions, e.g., buffers, temperature, time windows etc., is well known to the skilled person and may depend on the particular antibody as well as the food or feedstuff preparation to be analyzed. Preferred conditions are time windows are described in the accompanying Examples, below. As result of the first step, a complex will be present in the solution between the antibody of the invention and soy Gly m 8 protein, i.e. the antibody-soy Gly m8 protein complex. In some embodiments, these complex may be further purified from the remaining components of the aqueous solution, e.g., by immobilizing said complex and by carrying out washing steps.

The method for detecting in a further step comprises determining the antibody-soy Gly m8 protein complex formed upon specific binding of the antibody to the soy Gly m8 protein in step a). The complex may either be determined directly or indirectly. Direct detection may involve measurements of physico-chemical properties such as those measured by, e.g., Surface plasmon resonance (SPR) spectroscopy, Mass spectroscopy or NMR spectroscopy. Indirect detection, typically, involve a further detection agent that is used to detect the presence, absence or quantity of the complexes. Preferred agents are those which allow for specific detection by specific binding of the agent to the complex. Examples for such detection agents are antibodies that specifically bind to the complex as those specified elsewhere herein as well as aptamers or other specific binding agents. The skilled person is well aware of such agents. Details on preferred detection agents are also found in the accompanying Examples below. It will be understood that the detection agents are either directly coupled to a detectable as specified elsewhere herein or can be detected by yet a further detection agent. Suitable measures for detection and, thus, for qualitatively or quantitatively assessing the complexes present are well known in the art.

In a further step of the method, the soy material in the food preparations or feedstuff preparations will be detected if the antibody-soy Gly m8 protein complex was determined in step b). The method includes embodiments which merely detect the presence or absence of the antibody-soy Gly m8 protein complex and thereby the presence or absence of soy material in the preparations. However, also encompassed are embodiments where the amount of complexes is determined which allows for quantitatively determining the amount of soy material present in the preparations.

Preferably, said determining the antibody-soy Gly m8 protein complex comprises contacting the sample with a further antibody which specifically binds to the antibody of the invention, preferably, when present in the complex. More preferably, said further antibody has been linked to a detectable label or tag.

The term "further antibody" as used herein refers to an antibody which specifically binds to the antibody against soy Gly m 8 protein or to a complex between said antibody and soy Gly m 8 protein. How such an antibody, e.g., an anti-mouse monoclonal antibody, can be produced is well known in the art. Suitable antibodies are also described in the accompanying Examples, below. The said further antibody is, preferably, coupled to a detectable label as specified elsewhere herein.

Finally, the present invention contemplates a kit for carrying out the method of the present invention for detecting soy material in a food composition or feedstuff comprising the antibody of the invention, means for determining the presence or absence of the antibody-soy Gly m8 protein complex and, preferably, instructions for carrying out the said method.

The term "kit" as used herein refers to a collection of the aforementioned components, preferably, provided separately or within a single container. The container also comprises instructions for carrying out the method of the present invention. These instructions may be in the form of a manual or may be provided by a computer program code which is capable of carrying out the calculations and comparisons referred to in the methods of the present invention accordingly when implemented on a computer or a data processing device. The computer program code may be provided on a data storage medium or device such as a optical storage medium (e.g., a Compact Disc) or directly on a computer or data processing device. Moreover, the kit may, preferably, comprise standard amounts for the soy Gly m 8 protein from transgenic tobacco plants, e.g., for calibration purposes as described elsewhere herein.

In the following, particular embodiments of the present invention are summarized. However, these embodiments shall not be construed to limit the invention.

Embodiment 1: A method for the manufacture of an antibody that specifically binds to soy Gly m 8 protein wherein said method comprises:

a) immunising an animal with the purified soy Gly m8 protein, wherein said soy Gly m8 protein has been obtained by i) expressing soy Gly m8 protein in plants and, preferably, tobacco plants; and ii) purifying the soy Gly m8 protein from said plants and, preferably, tobacco plants; and b) obtaining an antibody from the animal which specifically bind to soy Gly m8 protein, wherein the animal will be sacrificed.

Embodiment 2: The method of embodiment 1, wherein said soy Gly m8 comprises the signal peptide and the pro-peptide of soy Gly m8.

Embodiment 3: The method of embodiment 1 or 2, wherein said soy Gly m8 protein further comprises a purification tag.

Embodiment 4: The method of any one of embodiments 1 to 3, wherein said soy Gly m8 protein is expressed from an expression construct that has been introduced into the tobacco plants and wherein the coding nucleic acid sequence for the soy Gly m8 protein has been codon-optimized for tobacco plants.

Embodiment 5: The method of any one of embodiments 1 to 4, wherein said purifying comprises at least one step of affinity purification of the soy Gly m8 protein and/or at least one step of size-exclusion purification of the soy Gly m8 protein.

Embodiment 6: The method of any one of embodiments 1 to 6, wherein said obtaining an antibody from the animal comprises generating hybridomas from the animal and selecting and cultivating a hybridoma clone which produces an antibody which specifically binds to soy Gly m8 protein.

Embodiment 7: The method of any one of embodiments 1 to 6, wherein said antibody has a KD of at least $1.57 \times 10^{-10}$ for the soy Gly m8 protein.

Embodiment 8: The method of any one of embodiments 1 to 7, wherein said antibody exhibits no cross reactivity for proteins from wheat, celery, mustard, peanut, black beans, mungo beans, white beans, quail beans, lupines, field bean and pea.

Embodiment 9: An antibody which specifically binds to soy Gly m8 protein wherein said antibody has been obtained by the method of any one of embodiments 1 to 8.

Embodiment 10: The antibody of embodiment 9, wherein said antibody is a monoclonal antibody.

Embodiment 11: Use of an antibody according to embodiment 9 or 10 for detecting the presence of soy material in a food preparation or feedstuff preparation.

Embodiment 12: A method for detecting soy material in a food preparation or feedstuff preparation comprising the steps of:

a) contacting a sample of the food preparation or feedstuff preparation with the antibody of embodiment 9 or 10 under conditions and for a time sufficient to allow specific binding of said antibody to soy Gly m8 protein comprised in the soy material; and b) determining the antibody-soy Gly m8 protein complex formed upon specific binding of the antibody to the soy Gly m8 protein in step a); and c) detecting the soy material in the food preparation or feedstuff preparation if the presence of the antibody-soy Gly m8 protein complex was determined in step b).

Embodiment 13: The method of embodiment 12, wherein said determining the antibody-soy Gly m8 protein complex comprises contacting the sample with a further antibody which specifically binds to the antibody of claim 9 or 10, preferably, when present in the complex.

Embodiment 14: The method of embodiment 13, wherein said further antibody has been linked to a detectable label or tag.

Embodiment 15: A kit for carrying out the method of any one of embodiments 12 to 14 comprising the antibody of embodiment 9 or 10, means for determining the presence or absence of the antibody-soy Gly m8 protein complex and, preferably, instructions for carrying out the said method.

All references cited in this specification are herewith incorporated by reference with respect to their entire disclosure content and the disclosure content specifically mentioned in this specification.

FIGURES

FIG. 1 shows the plant expression construct and purity and integrity of recombinant Gly m 8. (A) Schematic presentation (not to scale) of the expression cassette Gly m 8. SAR: scaffold attachment region; CaMV 35S promoter and terminator: promoter with duplicated enhancer and terminator of the Cauliflower mosaic virus (CaMV) 35S gene; 5' untranslated region: 5'-UTR of the chalcone synthase gene from *Petroselinum crispum* (CHS 5' UTR); Gly m 8: coding sequence for Gly m 8, UniProt ID 19594; His6 tag: six histidines affinity purification tag. (B) Schematic presentation (not to scale) of the Gly m 8 protein, including signal peptide (SP), pro-peptide (PP) and disulfide bond. (C) SDS-PAGE analysis of IMAC-purified Gly m 8 under reducing conditions. In lane 1 the molecular weight marker is shown. Crude filtered extracts of leaves of transiently transformed *N. bethamiana* (lane 2) were loaded onto IMAC columns and both flow-through and wash-out samples were collected (lane 3 and 4 respectively), in the eluate (lane 5) a protein band with the expected size of approximately 10 kDa was detected. (D) SDS-PAGE analysis of SEC-polished Gly m 8 under non-reducing (lane 2) and reducing (lane 3) conditions. A 99-% pure recombinant Gly m 8 protein was purified by SEC, which decomposes under reducing conditions into two subunits.

Figure 2:
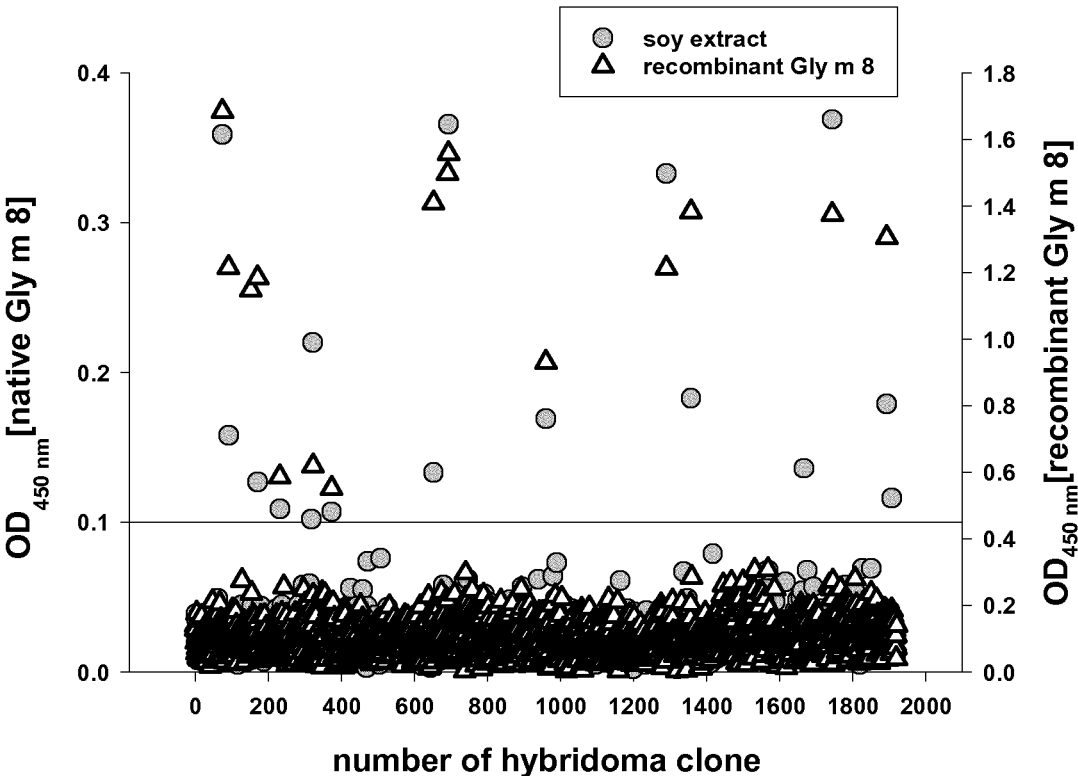

FIG. 2 shows the screening of antibody-producing hybridoma clones by indirect ELISA using plates coated with native or recombinant Gly m 8. Supernatants of hybridoma cultures were tested for containing Gly m 8-specific IgG antibodies which bound to both native (filled circle) and recombinant Gly m 8 (triangle) using an indirect ELISA. Binding of mAbs to the Gly m 8 antigen resulted in a high OD 450 nm signal as shown in the scatter blot of 2000 hybridoma clones. Read-outs higher than 0.1 OD point to high-affinity anti-Gly m 8 antibodies. Clones producing high-affinity antibodies were cryo-preserved and antibody-containing supernatants were collected for further analysis.

Figure 3:
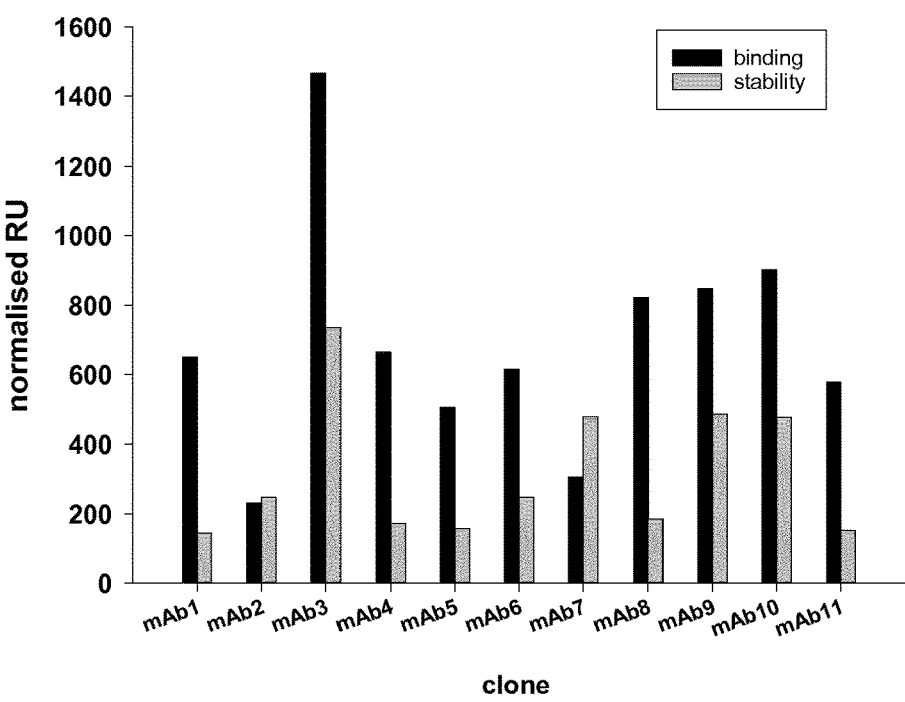
Figure 3:
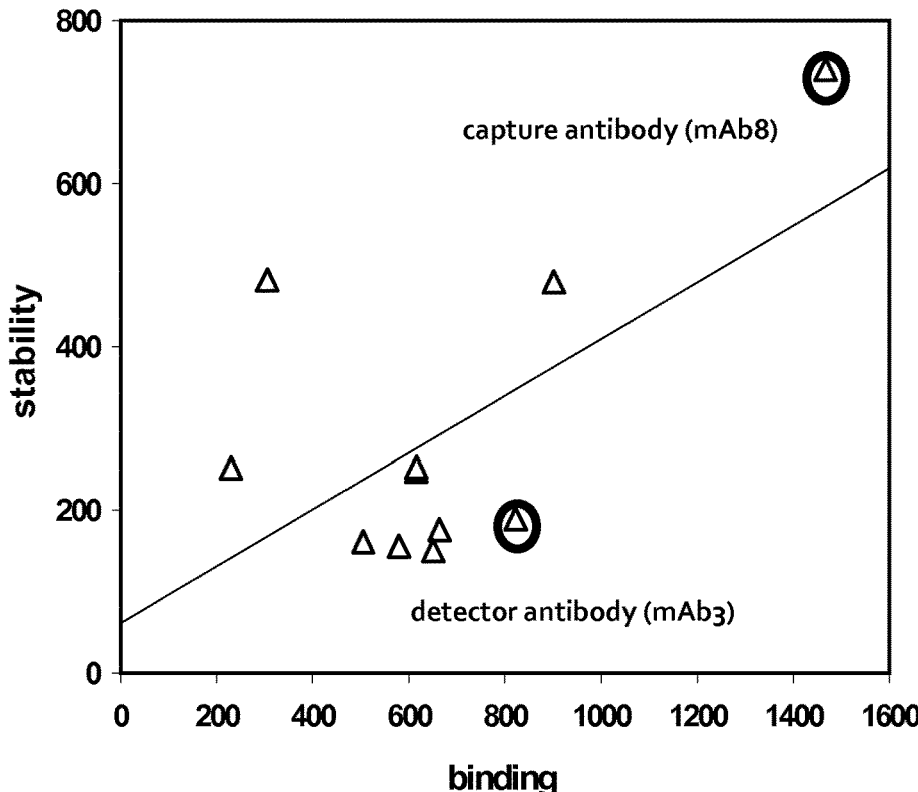

FIG. 3 shows Ranking of anti-Gly m 8 antibodies. Binding and stability of selected anti-Gly m 8 antibodies (mAb1 to mAb11) were tested on recombinant Gly m 8 conjugated onto the surface of a CM5 chip with the SPR biosensor instrument Biacore T200. Response units as indicator for specific binding of the antibody to the recombinant Gly m 8 covalently coupled to the solid phase at late binding and late stability report point are plotted (A). The lower plot (B) visualises these response units from the late association phase (binding) and late dissociation phase (stability) of 11 selected antibodies on a Gly m 8-captured surface in order to choose appropriate capture antibodies. The binding and binding stability are related to both association and dissociation rates of the interaction. The red encircled antibodies were used in the sandwich ELISA as capture (mAb3) or detection antibody (mAb8).

Figure 4:
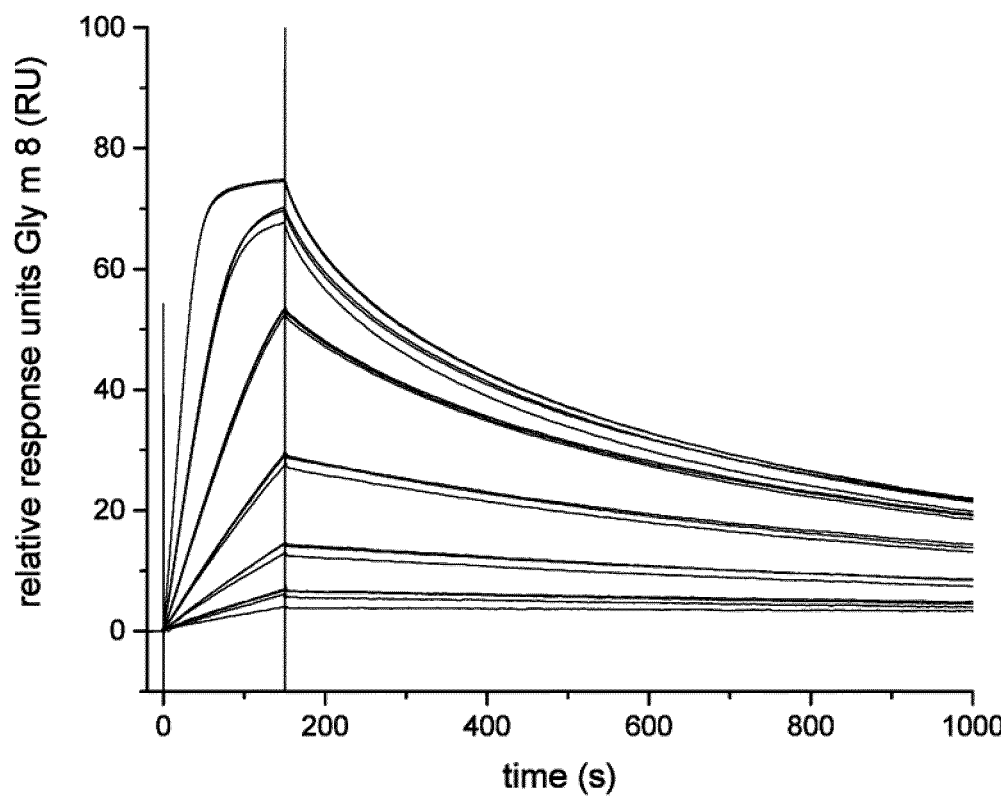

FIG. 4 shows exemplary sensorgrammes of SPR measurement for the kinetic analysis of the Gly m 8-specific mAb8. The affinity of the antibody mAb8 towards recombinant Gly m 8 was determined by SPR spectroscopy. For each cycle purified mAb8 was captured onto a Protein G-coated surface (500 response units (RU)). Subsequently, recombinant Gly m 8 was injected at concentrations of 5 nM, 2.5 nM, 1.25 nM, 0.625 nM, 0.3125 nM, or 0.15625 nM for 150 s to determine the on-rate (ka), dissociation was observed for 900 s to determine the off-rate (kd). The KD-values were estimated by fitting the data to interaction models using the Biacore T200 evaluation software applying the 1:1 Langmuir fit model.

Figure 5:
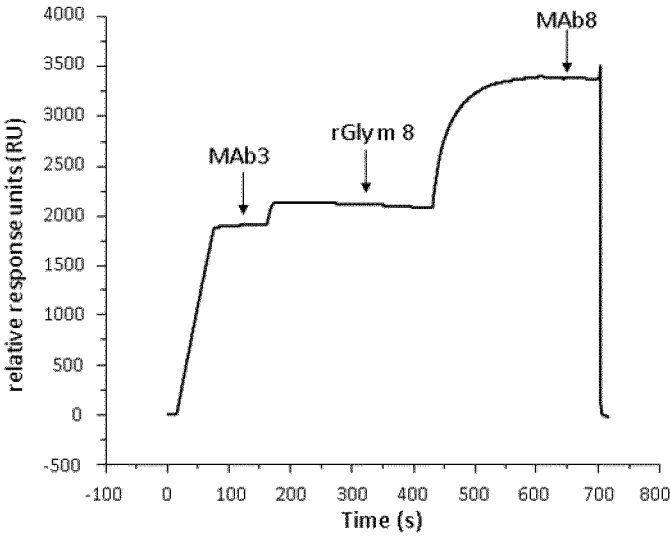

FIG. 5 shows a sensorgramme of SPR measurement to confirm simultaneous binding of mAb3 and mAb8 to recombinant Gly m 8. Since mAb8 represents murine IgG isotype IgG1 it binds only weakly to protein A, while mAb3 (IgG2A) can be efficiently captured on a Protein A functionalised CM5 sensor surface. Therefore, it was possible to illustrate the compatibility of the two Gly m 8-specific antibodies with a sandwich ELISA format in the context of a SPR experiment. The figure shows the subsequent injection of mAb3 (captured onto a Protein A surface), followed by recombinant Gly m 8 and finally mAb8. The comparable response unit levels obtained for the two antibodies 1500-1700 RU indicate that each molecule of recombinant Gly m 8 can be simultaneously recognised by both antibodies, confirming the suitability of the antibody combination in terms of the development of a sandwich ELISA for the quantification of Gly m 8.

Figure 6:
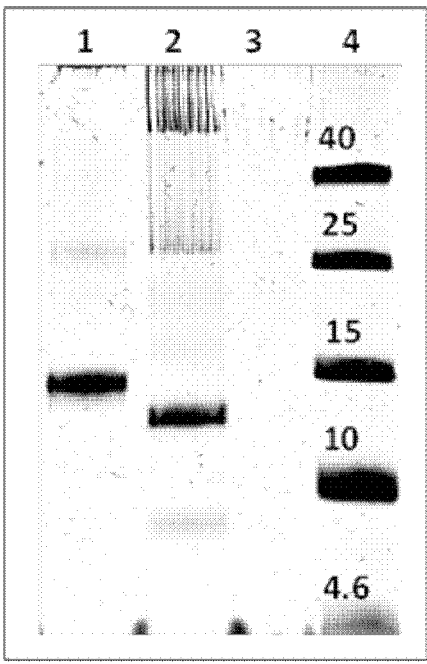

FIG. 6 shows a PAGE of native Gly m 8 isolated from soy extracts by immunoprecipitation with antibody anti-mAb3. Soy extract was incubated with anti-Gly m 8-3 antibody. Antibody was captured by protein G sepharose, washed and eluated by pH reduction to 3.7. Eluate was collected and separated on a 16% (w/v) tricine gel. Lane 1 represents the protein bands under non-reducing condition and lane 2 under reducing conditions. Lane 3 is empty and lane 4 shows the Spectra Multicolor Low Range Protein Ladder as calibration standard for estimating molecular weight of protein bands.

Figure 7:
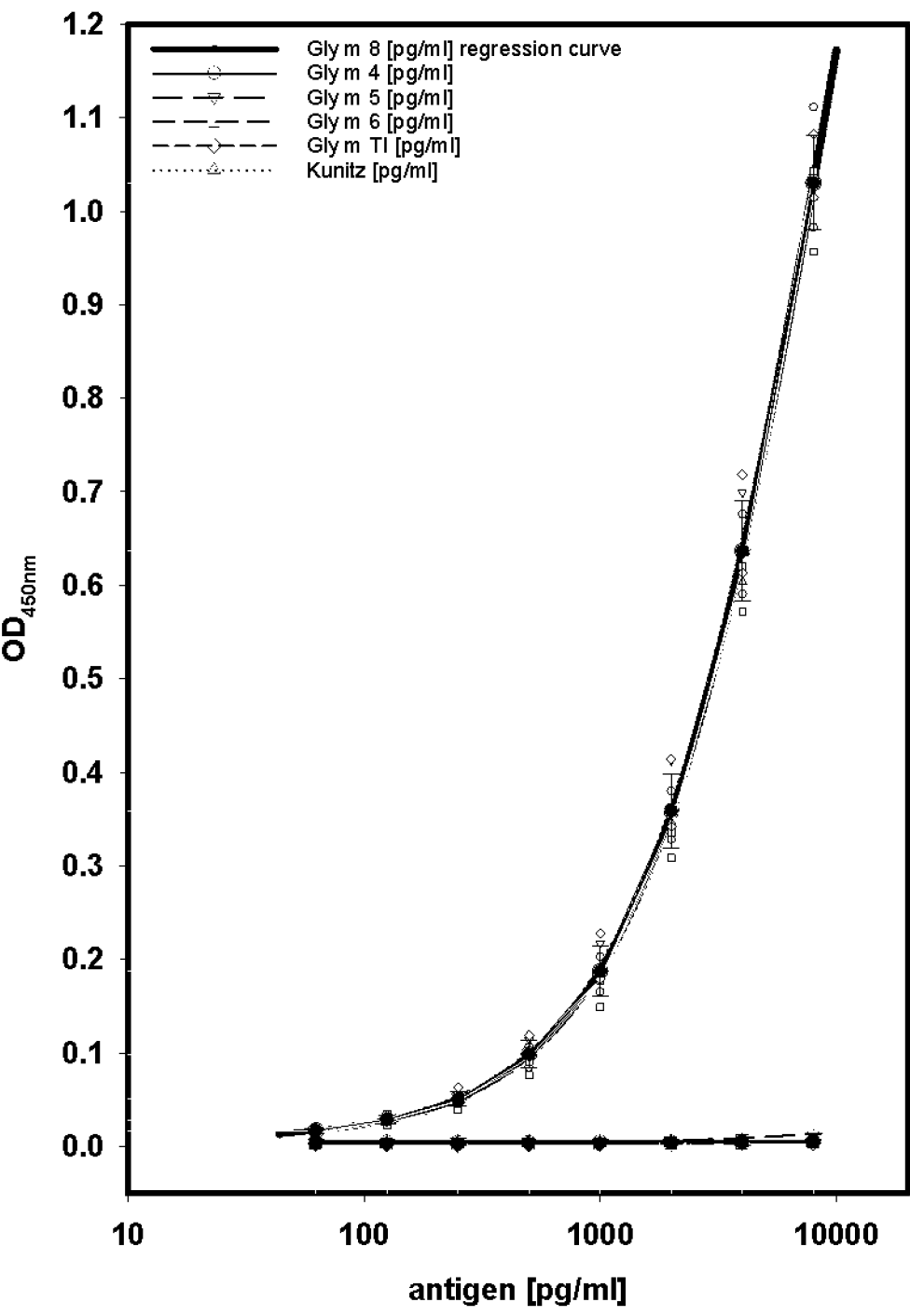

FIG. 7 shows a calibration curve of Gly m 8 ELISA. Representative calibration curves of the Gly m 8 sandwich ELISA are depicted in grey with the regression curve fitted by a four-parameter logistic model in red. LOD and LOQ as functions of the analytical specificity of Gly m 8 ELISA were determined by methodology in the linear and non-linear calibration cases on the basis of calibration curve (ISO 11843-5:2008). The blue curves represent the reaction of antibodies with potentially interfering proteins naturally being contained in whole soy extracts.

FIG. 8 shows (A) the codon-optimized DNA sequence for soy Gly m 8 (SEQ ID NO: 1) and (B) the amino acid sequence of soy Gly m 8 protein (SEQ ID No: 2).

EXAMPLES

Example 1: Production of Recombinant Soy Gly m 8 Protein in Tobacco Plants

Recombinant Gly m 8, which represents a soy storage molecule with a complex maturation cycle, was successfully produced in *N. benthamiana* by *Agrobacterium*-mediated transient expression. The native Gly m 8 sequence including the N-terminal signal peptide and pre-propeptide and a C-terminal His6 sequence was codon-optimised for expression in *N. benthamiana* and cloned into an expression cassette in the context of a binary plant expression vector (FIG. 1*a*). After proteolytic cleavage of the signal peptide and the pre-propeptide, the resulting mature native protein Gly m 8 consisted of two subunits joined by a disulfide bridge (FIG. 1B). Transient expression of Gly m 8 and subsequent IMAC and SEC purification yielded highly pure recombinant protein (FIG. 1*c*). During recombinant expression in the plant production host *N. benthamiana* Gly m 8 underwent the complete maturation cycle as demonstrated by reducing (two bands representing the processed subunits of 4.9 and 8.9 kDa) and non-reducing (one band representing the complex of the two covalently linked subunits at a size of 14 kDa) SDS-PAGE as shown in (FIG. 1*d*).

Plant Expression Construct

A synthetic gene coding for the precursor of Gly m 8 of *Glycine max* (UniProt ID: P19594) amino acids M1 to D158 including the signal peptide, the pro-peptide, and an additional his6-tag sequence at the 3'-terminus, was codon optimized for *Nicotiana benthamiana* from Geneart (Invitrogen, Carlsbad, CA). The synthetic gene was introduced through the NcoI/BamHI sites of the binary plant expression vector pTRAkt-ER (Sack et al. 2007, FASEB Journal 21(8): 1655-1664). The final construct pTRAkt_Gly m 8 was verified by sequencing.

Transient Gly m 8 Expression in Plants

The pTRAkt_Gly m 8 vector was propagated in *E. coli* DH5☐ cells (NEB, Frankfurt/Main, Germany), purified, introduced into electrocompetent *Agrobacterium tumefaciens* cells and used for transient expression in *N. benthamiana* plants as previously described (Feller et al. 2013PloS one 8(11), e79920).

Purification of Plant-Produced Gly m 8

Extraction and immobilised metal affinity chromatography (IMAC) purification of plant-derived Gly m 8 was performed as previously described using standard procedures (Feller et al., 2013, loc. cit.). Afterwards, the Gly m 8 was further purified by size exclusion chromatography (SEC) using a Superdex75 16/60 (GE Healthcare, Freiburg, Germany). Integrity and purity of the recombinant Gly m 8 was verified by SDS-PAGE and LC/MS-MS analysis).

Example 2: Generation and Characteristics of Monoclonal Antibodies Against Soy Gly m 8 Protein Immunisation of mice with recombinant Gly m 8 protein revealed antibodies which display high-affinity binding to both recombinant and native protein. The latter was captured as whole aqueous soy extract in indirect ELISA (FIG. 2). Ten antibodies, showing no cross-reactivity against protein extracts isolated from legume crops, pea, peanut, and lupine, were pre-selected to develop a sandwich ELISA. Ranking of antibodies according to their binding and stability on recombinant Gly m 8 covalently conjugated onto the surface of Biacore CM 5 chips led to the selection of two elite mAbs—anti-Gly m 8-3 (mAb3) and anti-Gly m 8-8 (mAb8) (FIG. 3). Both mAbs were further characterised by kinetic analysis (FIGS. 4 and 5). The KDs of both mAbs were in the sub-nanomolar range (KD mAb3: 3.92×10-10, KD mAb8: 1.57×10-10 (FIG. 5 and Table 2) demonstrating their high binding affinity. Additionally, the capture antibody mAb8 was characterised by immunoprecipitation of native soy extract with protein G sepharose. The resulting immunoprecipitate was analysed by PAGE and formed two main protein species with molecular weights of 25 kDa and 15 kDa under non-reducing conditions (FIG. 6). LC-MS/MS analysis confirmed the 25-kDa protein as to be mouse kappa light chain originating from mAb3 (score 331, Uniprot P01837) and the 15-kDa protein as Gly m 8 with a score of 896.03 (Uniprot ID P19594). Under non-reducing conditions this main 15-kDa protein band shifted into two bands of about 11 kDa and 5 kDa (FIG. 6), demonstrating the linkage of the two subunits by disulphide bonds. The LC-MS/MS data proved the specific binding of mAb8 to Gly m 8. In addition, no cross-reactivity of mAb3 and mAb8 could be observed in both indirect (screening) ELISA and sandwich ELISA as well with extracts derived from wheat, celery, different mustards, black beans, mungo beans, white beans, quail beans, lupine, peanut, *Pisum sativum*, and field bean (*Vicia faber*).

Generation of Monoclonal Antibodies

Mouse anti-Gly m 8 mAbs were generated by immunising female B ALB/c mice (Janvier Labs, Le Genest-Saint-Is1, Lrance) with plant-produced and IMAC/SEC-purified recombinant Gly m 8 protein. The immunisation experiments were approved by the State Animal Care and Use Committee (Landesdirektion Sachsen, Leipzig, Germany, V 07/14) and were carried out in accordance with the European Communities Council Directive (86/609/EEC) for the Care and Use of Laboratory Animals. The mouse with the highest Gly m 8-specific antibody titer was used as donor of spleenocytes, which were fused to X63.Ag8.653 myeloma cells (ACC 43, DSMZ, Braunschweig, Germany). Hybridoma supernatants were screened by indirect ELISA on flat-bottom high protein-binding capacity 96-well ELISA plates (Nunc MaxiSorp™, Thermo Fisher Scientific Life Technologies, Darmstadt, Germany) coated with either recombinant protein (2 µg/rnl) or whole soy extract (10 µg/ml). Two of these hybridomas were deposited on Aug. 13, 2025, under the provisions of the Budapest Treaty on the International Recognition of the Deposit of Microorganisms for the Purposes of Patent Procedure at the Deutsche Sammlung von Mikroorganismen und Zellkulturen, Inhoffenstrasse 7B, 38124 Braunschweig, Science Campus Braunschweig-Süd, Germany (DSMZ) under Accession Numbers DSM ACC3383 and DSM ACC3383. Cross-reactivity of generated IgG antibodies to other legumes (lupine, pea nut and pea) was identified by ELISA using total protein extracts (total protein concentration=10 µg/rnl) from the corresponding plant seeds.

Surface Plasmon Resonance (SPR) Spectroscopy

Ten IgG-positive clones were selected for SPR analysis on covalently coupled purified recombinant Gly m 8 protein using a Biacore T200 SPR biosensor instrument (GE Healthcare, Freiburg, Germany) previously described based on an Fc-specific antibody capture system.

Calibration Free Concentration Analysis (CFCA)

CFCA, a method described elsewhere, was performed to determine the active concentration of recombinantly produced and purified Gly m 8 using a Biacore T200 instrument (GE Healthcare) and a CM5-S-Series sensor chip with recombinant Protein A prepared as described previously (Boes et al., 2011). These measurements were performed at 25° C. using HBS-EP (10 mM (4-(2-hydroxyethyl)-1-piperazineethanesulfonic acid), 150 mM NaCl, 3 mM EDTA, 0.005% (w/v) polysorbat-20) as running buffer. A 1-min pulse with 30 mM HCl regenerated surfaces.

To ensure a sufficiently fast initial binding rate, 2500 response units (RU) of the Gly m 8 specific murine mAb3 were captured in each assay step. Purified recombinant Gly m 8 was used at three different dilutions (1/3000, 1/4500 and 1/6000) to ensure an initial binding rate (IBR) between 0.5 and 5 RU/s at a flow rate of 5 µl/min. IBR was measured at 5 and 100 µl/min using double referencing. Antigen-specific antibody concentration was determined using the CFCA module of the Biacore T200 Evaluation Software (GE Healthcare). A molecular weight of 16,000 kDa and a diffusion coefficient of 9.16×10-11 m2/s were used in the binding model.

Kinetic Analysis

Kinetic analysis of the Gly m 8-specific mouse anti-Gly m 8-3 (mAb3, produced by the hybridoma deposited at the DSMZ under Accession Number DSM ACC3383) and mouse anti-Gly m 8-8 (mAb8, produced by the hybridoma deposited at the DSMZ under Accession Number DSM ACC3384) were carried out using the Biacore T200 instrument. Therefore, ca. 500 RU of mAb8 were captured onto an anti-mouse-coated CM5 chip prepared with a mouse antibody capture kit (GE Healthcare). Mab3 were captured on a Protein A surface prepared as described elsewhere. To determine the kinetic binding constants purified recombinant Gly m 8 was injected at a flow rate of 30 m 1/m in for 150 s (mAb8) or 180 s (mAb3), respectively. Then, dissociation followed for 900 s (mAb8) or 400 s (mAb3), respectively. Gly m 8 was used at the following CFCA-based concentrations (5 nM, 2.5 nM, 1.25 nM, 0.625 nM, 0.3125 nM, or 0.15625 nM). Between measurements the surface was regenerated by pulsing for 1 min with 10 mM glycine/HCl. Buffer injections were used for double referencing. Binding curves were evaluated using Biacore T200 Evaluation Software (GE Healthcare) applying a 1:1 binding model.

Sandwich Assay

To confirm simultaneous binding of mAb3 and mAb8 a sandwich assay was performed. Anti-Gly m 8 mAb3 was captured on a Protein A-functionalised surface and saturated with recombinant Gly m 8. Afterwards mAb8 was injected to illustrate the binding of mAb8 to Gly m 8 captured by mAb3.

Example 3: ELISA for Soy Material Detection

Features of the developed Gly m 8 sandwich ELISA are lower limit of detection (LOD>10 pg/ml determined by the average values of 10 matrix-blanks plus three standard deviations) and LOQ=65 pg/ml, determined as lowest concentration of spiked Gly m 8 in three different matrices or buffer as well that is still reliably detectable. We determined the inter-assay variance (robustness) by analysing the same samples on three different days by two different operators (FIG. 7). The precision of the assay was proved by ten technical replicates of three different samples. When spiking recombinant Gly m 8 into three different matrices recovery rates reached 98 to 109% (Tab.3). Gly m 8 was detectable in all investigated foods and food ingredients. In complexly processed food the recovery rates were calculated on the basis of manufacturer's specification.

Quantification of Gly m 8 was performed by sandwich ELISA using two out of the 10 pre-selected antibodies. Capture antibodies were immobilised onto 96-well plates (Nunc MaxiSorp™, Thermo Fisher Scientific Life Technologies) in 0.5 M carbonate buffer at 4° C. overnight. Plates were washed three times with phosphate-buffered saline 154 mM NaCl, 0.05% Tween (PBS-T) and blocked with Superblock™ blocking reagent (Thermo Fisher Scientific Life Technologies). Afterwards, a one-hour incubation at ambient temperature with liquid plate sealer (Candor BioScience, Wangen, Germany) followed and plates were air-dried and shrink-wrapped and stored at ambient temperature.

Extracted samples were incubated for 10 min at ambient temperature (RT) in duplicate. After a further washing step (3×PBS-T), horseradish peroxidase (POD)-conjugated detection antibody was incubated for 10 min at RT. POD activity as an indicator for bound sample was determined following a third washing step (3×PBS-T) by incubating the plate with TMB-E substrate (3,3',5,5'-tetramethybenzidine) (DUNN Labortechnik, Asbach, Germany). A yellow colour results after acidification using 0.5 M sulphuric acid. Colour intensity represents a signal for bound detection antibodies and was measured at 450 nm. Signal intensities were calculated by extrapolation to a calibration curve from purified recombinant protein consisting of eight known concentrations. ELISA was validated according to AOAC guidelines, Appendix M, referenced to Abbott et al (Abbott et al. 2010 Journal of AOAC International 93 (2), S. 442-450) and DIN 15011843-5.

Limit of Detection and Recovery

Limit of detection was determined measuring eight different concentrations of purified recombinant Gly m 8 in extraction buffer. Recovery was calculated by spiking five different concentrations of recombinant Gly m 8 into three different matrices relevant for processed soy, almond-wheat-muffin, rice cookie and minced boiled sausage. Lower limit of detection (LOD) and Lower Limit of Quantification (LOQ) were calculated by checking sensitivity and specificity using the methodology in the linear and non-linear calibration cases (ISO 11843-5:2008).

Precision and Robustness of the Test

The ability of the anti-Gly m 8 sandwich ELISA to resist changes in results due to minor deviations in experimental procedure were tested by deviations in time (two times+10% of recommended time of 10 min), volume (two volumes+10% of set volume 100 μl) and temperature (ambient temperature, 20° C., 28° C., and 37° C.), respectively. Furthermore, two different individuals performed the test on three different days.

Specificity and Selectivity

Specificity of the antibodies as the ability to bind the antigen in presence of components which may be present was tested by using recombinant Gly m 4 and recombinant Gly m TI and Gly m 6 and Gly m 5 (Sigma Aldrich, Deisenhofen, Germany). Selectivity of the antibodies as the extent to which they can bind the antigen in complex mixtures interference was tested using three different matrices.

Sample Extraction

Samples, listed in Table 1 (3.3 mg/ml) were extracted by homogenizing and mixing 30 min in PBS (300 mM NaCl) at ambient temperature. Samples listed in Table 1 were used.

Purification of Native Gly m 8 Antigen by Immunoprecipitation

Extracts of hexane defatted soy flakes (prepared as previously described by Meinlschmidt et al. 2016, Food science & nutrition 4 (1), S. 11-23) were pre-incubated with 0.5 ml protein G sepharose 4 Fast Flow (90-μm particle size, GE Healthcare) 1 h at room temperature. Afterwards, protein G sepharose was removed by filtration through a disposable polypropylene device with polyethylene filter (30 μm, Thermo Fisher Scientific Life Technologies). Pre-adsorbed protein extract was incubated with anti-Gly m 8 mAb3 antibody (ELISA capture antibody) for 1 h at room temperature on a tube rotator (Stuart Tube Rotator SB3, Cole-Parmer, Wertheim, Germany). After this incubation, 1 ml of protein G sepharose 4 Fast Flow (90-μm particle size, GE Healthcare) was added and mixed by rotating was continued 1 h at room temperature. The mixture was filtered through a disposable polypropylene device with polyethylene filter (30 μm, Thermo Fisher Scientific Life Technologies) forming a column matrix by gravity flow. This protein G sepharose—column was washed ten times with 10 ml PBS each and eluted with 0.5 ml glycin-HCl (0.1 M, pH 3.6). The column eluate was neutralised with 50 μl Tris (1 M, pH 9.0) and analysed by polyacrylamide gel electrophoresis (PAGE).

Proteins were separated in 16% (w/v) tricine gels and protein bands were analysed by LC-MS/MS analysis as described previously (Meinlschmidt et al. 2017, Innovative Food Science & Emerging Technologies 40, S. 58-67.).

Discussion

The main challenge for detecting allergens in food by ELISA is the reliable protein isolation during sample preparation from complex food matrices. Limited solubility, mainly of globulins in legume extracts, significantly influences the reliability of results as previously shown for the two main storage proteins Gly m 5 and Gly m 6 in soy. Therefore, for allergen tests targeting soluble proteins such as albumins, which remain stable against different proteases and heat exposition and maintain the solubility of the untreated native protein due to their unique three-dimensional structure is desirable. In addition, albumins exhibit less cross-reactivity between different legumes species whereas 115 globulins, which are often used as antigens in ELISA, do due to their high sequence homology finally leading to considerable constraints in ELISA detection which was already reported by other authors using a Gly m 6 ELISA derived from R-Biopharm (Darmstadt, Germany) (Lacorn et al. 2016, loc. cit.). According to the dendrogram of sequence homology among the 2S albumins only the 2S albumins of lupine (i.e. delta conGlytin) and peanut (i.e. Ara h6) are considered to be cross-reactive to Gly m 8. However, no cross-reactivity of Gly m 8-specific mAb3 and mAb8 to these legumes was determined. The other main storage protein Gly m 5 (7S globulin) displays less sequence homologies to equivalents in other legumes. However, the detection of Gly m 5 requires labour-intensive heat extraction for maximal recovery which represents a disadvantage of this approach (Pavlicevic et al. 2013, Hem Ind 67 (4), S. 687-694).

A key advantage of the Gly m 8 sandwich ELISA presented herein is the high affinity of the applied antibodies, which allow binding of the Gly m 8 antigen at very low concentrations and the particular high charcterization level of the antibodies by SPR analysis. The typical binding and stability characteristics of mAbs in SPR experiments enables a stringent quality control of produced antibody charges. Vice versa a systematic quality control of the recombinant Gly m 8 calibrator with antibodies of the same fusion, but not used in ELISA, is possible.

The utilization of Gly m 8 as marker antigen for detection and quantification of soy allergen in food exhibits a second important advantage. It has been shown being the most important predictor for severity of allergic reactions in children so far (Ebisawa et al. 2013, loc. cit.). However, in case of Gly m 8 a discrepancy in the assessment of its allergenicity in different studies exists, while only Ebisawa and colleagues used native Gly m 8 which was coupled to an immunocap device. Both other studies used either recombinant protein produced in *E. coli* (Lin et al. 2006, International archives of allergy and immunology 141 (2), S. 91-102) or microarrays with overlapping peptides representing solely linear epitopes being incapable of reflecting the three-dimensional structure of the protein.

Finally, the Gly m 8 ELISA is also advantageous to obtain information on the allergenic potential of processed soy proteins regarding this allergenic ingredient. In general the performance of a commercial ELISA in food analyses is evaluated as reliable if recovery rates in processed food are in the range between 50 and 150% (Abbott et al. 2010). Therefore, the newly presented Gly m 8 ELISA would be most suitable in applications intending detection of soy ingredients in chocolate or most texturized vegetable protein (TVP) detection besides native soy protein (Tab. 4). Keeping in mind that only 1.1 mg in 1 g soy protein are Gly m 8 compared to 300 to 600 mg Gly m 5 or Gly m 6 in 1 g soy, respectively, the sensitivity of the new Gly m 8 ELISA is amazingly high.

The test described herein was able to detect minimal soy amounts in both rice cookie and minced boiled sausages which were otherwise not detectable in native extractions using other test systems such as different Gly m TI ELISAs despite Gly m TI represents 60 mg of 1 g soy protein.

In summary, the Gly m 8 ELISA introduced in this study combines the advantages of monoclonal antibodies, which are nearly unlimited available, and a rugged highly purified recombinant standard, that could be utilized as reference material in uniform and stable quality.

TABLE 1

Soy-containing foods and food-ingredients.
Commercial soy products, samples of previous proficiency tests
and in-house soy processed food were used as samples

| Sample | Manufacturer/provider |
| --- | --- |
| Soy flake | In-house flakes prepared at Fraunhofer IVV from untoasted soybeans (Glycine max (L.) Merr.) from Naturkost Ernst Weber (Munich, Germany) |
| Soy protein isolate | Wilcon G100, Wilmar, Singapore |
| Texturized vegetable protein | different manufacturers, for example GutBio, (France) 43-49% protein |
| TOFU | different manufacturers, for example Alnatura (Bickenbach, Germany) and Tofu Life (Hillersheim, Germany), 12.5-16.7% protein |
| Minced boiled sausage | LVU Durchführung von Labor-vergleichsuntersuchungen (Herbolzheim, Germany) |

TABLE 1-continued

Soy-containing foods and food-ingredients.
Commercial soy products, samples of previous proficiency tests
and in-house soy processed food were used as samples

| Sample | Manufacturer/provider |
| --- | --- |
| Rice cookies | LVU Durchführung von Labor-vergleichsuntersuchungen (Herbolzheim, Germany) |
| Roasted soy bean | Seeberger (Ulm, Germany) |
| Model chocolate containing 1% (w/v) soy | Ifp Institut für Produktsicherheit, Berlin, Germany, in-house production |
| Model cookie containing 1% (w/v) soy | Ifp Institut für Produktsicherheit, Berlin, Germany, in-house production |
| Soy milk | Alpro soya light 2.1% (v/v) protein (Wevelgem, Belgium,) |

TABLE 2

Kinetic parameters derived from SPR-based interaction analysis
Kinetic parameters ka, kd, and KD were derived by analysis of binding
curves at 6 concentrations of recombinant Gly m 8. Exemplary
sensogramme shown in FIG. 4.

| Sample | $k_a$ [$M^{-1} s^{-1}$] | $SE(k_a)$ [$M^{-1} s^{-1}$] | $k_d$ [$s^{-1}$] | $SE(k_{di})$ [$s^{-1}$] | KD [M] |
| --- | --- | --- | --- | --- | --- |
| mAb8 | $3.76 \times 10^7$ | $1.6 \times 10^5$ | $5.89 \times 10^{-3}$ | $2.5 \times 10^{-5}$ | $1.57 \times 10^{-10}$ |
| mAb3 | $1.74 \times 10^7$ | $1.1 \times 10^5$ | $6.7 \times 10^{-3}$ | $2.5 \times 10^{-5}$ | $3.92 \times 10^{-10}$ |

TABLE 3

Recovery of recombinant Gly m 8 at five different
concentration levels in three different matrices.
Matrices produced by extraction of indicated processed food were spiked
with recombinant Gly m 8 protein and the recovery rates in percent of
the spiked amount were measured by Gly m 8 sandwich ELISA.

| Spiked Gly m 8 [pg/ml] | Recovery in almond muffin matrix [%] | Recovery in minced boiled sausage matrix [%] | Recovery in rice cookie- matrix [%] | Recovery in extraction buffer [%] |
| --- | --- | --- | --- | --- |
| 5000 | 104 +/– 4.5 | 108 +/– 4.6 | 110 +/– 12.2 | 101 +/– 5.9 |
| 2500 | 101 +/– 4.6 | 104 +/– 6.7 | 109 +/– 11.9 | 109 +/– 15.0 |
| 500 | 99 +/– 7.8 | 108 +/– 5.9 | 106 +/– 13.4 | 109 +/– 15.1 |
| 100 | 95 +/– 14.7 | 99 +/– 9.0 | 98 +/– 18.4 | 103 +/– 16.1 |
| 65 | 97 +/– 10.3 | 105 +/– 10.9 | 99 +/– 20.4 | 107 +/– 23.2 |

TABLE 4

Amount of Gly m 8 measured in processed food as indicated.
Measured concentrations of Gly m 8 in ELISA using a four-parameter logistic analysis
are given in pg/ml. Additional maximal level of dilution and amounts in pg in 300 mg
sample are shown. Recovery rates were calculated illustrative, provided that 1 g soy
protein contains 1 mg Gly m 8 and referred to protein content according to
manufacturer's specification.

| Food/Food ingredient | Measured concentration [pg/ml] | Maximal dilution factor | Mean amount [pg] in 300 mg original sample weight | Protein content [%] | Recovery in relation to total soy protein |
| --- | --- | --- | --- | --- | --- |
| Soy flake | 5,803 | 512,000 | $580 \times 10^6$ | 45 | 429 |
| Soy protein isolate | 34,426 | 5,120,000 | $342 \times 10^6$ | 16.7 | 380 |
| Texturized vegetable protein | 1,307 | 128,000 | $130 \times 10^6$ | 43 | 100 |
| TOFU | 159 | 16,000– | $9.3 \times 10^6$ | 13.3 | 23.3 |
| Minced boiled sausage | (11, <LQL) | 5 | | | |
| Rice cookies | 126 | 5 | 632 | 0.002 | 23.5 |

TABLE 4-continued

Amount of Gly m 8 measured in processed food as indicated.
Measured concentrations of Gly m 8 in ELISA using a four-parameter logistic analysis
are given in pg/ml. Additional maximal level of dilution and amounts in pg in 300 mg
sample are shown. Recovery rates were calculated illustrative, provided that 1 g soy
protein contains 1 mg Gly m 8 and referred to protein content according to
manufacturer's specification.

| Food/Food ingredient | Measured concentration [pg/ml] | Maximal dilution factor | Mean amount [pg] in 300 mg original sample weight | Protein content [%] | Recovery in relation to total soy protein |
|---|---|---|---|---|---|
| Roasted soy bean | 5,358 | 2,000 | $9.954 \times 10^6$ | 45 | 7.3 |
| Model chocolate containing 1% soy | 829 | 2,000 | $1.59 \times 10^6$ | 1 | 100 |
| Model cookie containing 1% soy | 425 | 500 | $2.5 \times 10^6$ | 1 | 177 |
| Soy milk | 405 | 156,250 | | | |

What is claimed is:

1. A method for the manufacture of an antibody that specifically binds to soy Gly m8 protein wherein said method comprises:
   a) immunizing an animal with purified soy Gly m8 protein, wherein said soy Gly m8 protein has been obtained by:
      i) transiently expressing soy Gly m8 protein in plants; and
      ii) purifying the soy Gly m8 protein from said plants; and
   b) obtaining an antibody from the animal which specifically binds to soy Gly m8 protein,
   wherein the obtaining an antibody from the animal comprises generating hybridoma clones from the animal and selecting and cultivating a hybridoma clone that produces an antibody that specifically binds to soy Gly m8 protein, wherein the antibody has a KD of at least $1.57 \times 10^{-10}$ for the soy Gly m8 protein, and wherein the antibody is selected from the group consisting of mAb3 produced by hybridoma mouse anti-Gly m 8-3 deposited at the Deutsche Sammlung von Mikroorganismen und Zellkulturen (DSMZ) under Accession Number DSM ACC3383 and mAb8 produced by hybridoma mouse anti-Gly m 8-8 deposited at the Deutsche Sammlung von Mikroorganismen und Zellkulturen (DSMZ) under Accession Number DSM ACC3384.

2. The method of claim 1, wherein said soy Gly m8 comprises a signal peptide and a pro-peptide of soy Gly m8.

3. The method of claim 1, wherein said soy Gly m8 protein further comprises a purification tag.

4. The method of claim 1, wherein said soy Gly m8 protein is expressed from an expression construct that has been introduced into the tobacco plants and wherein the coding nucleic acid sequence for the soy Gly m8 protein has been codon-optimized for tobacco plants.

5. The method of claim 1, wherein said purifying comprises at least one step of affinity purification of the soy Gly m8 protein and/or at least one step of size-exclusion purification of the soy Gly m8 protein.

6. The method of claim 1, wherein the soy Gly m8 protein is expressed in tobacco plants.

7. An antibody which specifically binds to soy Gly m8 protein wherein said antibody is selected from the group consisting of mAb3 produced by hybridoma mouse anti-Gly m 8-3 deposited at the Deutsche Sammlung von Mikroorganismen und Zellkulturen (DSMZ) under Accession Number DSM ACC3383 and mAb8 produced by hybridoma mouse anti-Gly m 8-8 deposited at the Deutsche Sammlung von Mikroorganismen und Zellkulturen (DSMZ) under Accession Number DSM ACC3384.

8. A method for detecting soy material in a food preparation or feedstuff preparation comprising the steps of:
   a) contacting a sample of the food preparation or feedstuff preparation with the antibody of claim 1 under conditions and for a time sufficient to allow specific binding of said antibody to soy Gly m8 protein comprised in the soy material; and
   b) determining the antibody-soy Gly m8 protein complex formed upon specific binding of the antibody to the soy Gly m8 protein in step a); and
   c) detecting soy material in the food preparation or feedstuff preparation if the presence of the antibody-soy Gly m8 protein complex was determined in step b).

9. The method of claim 8, wherein said determining the antibody-soy Gly m8 protein complex comprises contacting the sample with a further antibody which specifically binds to the antibody which specifically binds to soy Gly m8 protein.

10. The method of claim 9, wherein said further antibody has been linked to a detectable label or tag.

11. The method of claim 9, wherein said further antibody specifically binds to the antibody which specifically binds to soy Gly m8 protein when said antibody which specifically binds to soy Gly m8 protein is present in said complex.

12. A kit for carrying out a method for detecting soy material in a food preparation or feedstuff preparation, comprising the antibody of claim 7 and means for determining the presence or absence of antibody-soy Gly m8 protein complex.

* * * * *

SEQUENCE LISTING

<160> NUMBER OF SEQ ID NOS: 2

<210> SEQ ID NO 1
<211> LENGTH: 477
<212> TYPE: DNA
<213> ORGANISM: Glycine max
<220> FEATURE:
<221> NAME/KEY: misc_feature
<222> LOCATION: (1)..(477)
<223> OTHER INFORMATION: Gly m 8 codon-optimzed cDNA sequences

<400> SEQUENCE: 1
atgggcacca agttcacaat cctcctcatc tctcttctct tctgcatcgc ccacacttgc      60
agcgcctcca aatggcagca ccagcaagat agctgccgca agcagctcca gggggtgaac     120
ctcacgccct gcgagaagca catcatggag aagatccaag gccgcggcga tgacgatgat     180
gatgatgacg acgacaatca cattctcagg accatgcggg gaagaatcaa ctacataagg     240
aggaacgaag gaaaagacga agacgaagaa gaagaaggac acatgcagaa gtgctgcaca     300
gaaatgagcg agctgagaag ccccaaatgc cagtgcaaag cgctgcagaa gataatggag     360
aaccagagcg aggaactgga ggagaagcag aagaagaaaa tggagaagga gctcattaac     420
ttggctacta tgtgcaggtt tggacccatg atccagtgcg acttgtcctc cgatgac         477

<210> SEQ ID NO 2
<211> LENGTH: 158
<212> TYPE: PRT
<213> ORGANISM: Glycine max

<400> SEQUENCE: 2

Met Thr Lys Phe Thr Ile Leu Leu Ile Ser Leu Leu Phe Cys Ile Ala
1               5                   10                  15

His Thr Cys Ser Ala Ser Lys Trp Gln His Gln Gln Asp Ser Cys Arg
            20                  25                  30

Lys Gln Leu Gln Gly Val Asn Leu Thr Pro Cys Glu Lys His Ile Met
        35                  40                  45

Glu Lys Ile Gln Gly Arg Gly Asp Asp Asp Asp Asp Asp Asp Asp Asp
    50                  55                  60

Asn His Ile Leu Arg Thr Met Arg Gly Arg Ile Asn Tyr Ile Arg Arg

-continued

```
65                    70                    75                    80

Asn Glu Gly Lys Asp Glu Asp Glu Glu Glu Glu Gly His Met Gln Lys
                85                    90                    95

Cys Cys Thr Glu Met Ser Glu Leu Arg Ser Pro Lys Cys Gln Cys Lys
            100                   105                   110

Ala Leu Gln Lys Ile Met Glu Asn Gln Ser Glu Glu Leu Glu Glu Lys
        115                   120                   125

Gln Lys Lys Lys Met Glu Lys Glu Leu Ile Asn Leu Ala Thr Met Cys
    130                   135                   140

Arg Phe Gly Pro Met Ile Gln Cys Asp Leu Ser Ser Asp Asp
145                   150                   155
```